(12) United States Patent
Burgmeier et al.

(10) Patent No.: US 8,641,982 B2
(45) Date of Patent: Feb. 4, 2014

(54) VAPORIZER FOR STERILIZATION OF PLASTIC CONTAINERS

(75) Inventors: Berthold Burgmeier, Eglingen (DE); Patrick Engelhard, Elsendorf (DE); Josef Knott, Schierling (DE)

(73) Assignee: Krones AG (DE)

( * ) Notice: Subject to any disclaimer, the term of this patent is extended or adjusted under 35 U.S.C. 154(b) by 699 days.

(21) Appl. No.: 12/670,600

(22) PCT Filed: Jul. 18, 2008

(86) PCT No.: PCT/EP2008/059421
§ 371 (c)(1),
(2), (4) Date: Mar. 1, 2010

(87) PCT Pub. No.: WO2009/013226
PCT Pub. Date: Jan. 29, 2009

(65) Prior Publication Data
US 2010/0202919 A1 Aug. 12, 2010

(30) Foreign Application Priority Data

Jul. 23, 2007 (DE) .......................... 10 2007 034 205

(51) Int. Cl.
*A61L 9/00* (2006.01)
*F26B 13/10* (2006.01)
*B08B 3/00* (2006.01)
*B65B 43/42* (2006.01)

(52) U.S. Cl.
USPC ............. 422/298; 422/305; 422/307; 34/523; 261/78.1; 134/105; 141/82

(58) Field of Classification Search
USPC .......... 122/5.52, 451.1; 34/523; 261/76, 78.1; 422/28, 125, 298–300, 305, 307; 134/90, 105, 136, 166 R, 170; 141/82
See application file for complete search history.

(56) References Cited

U.S. PATENT DOCUMENTS

| 4,631,173 A | 12/1986 | Müller et al. ................... 422/28 |
| 5,068,087 A | 11/1991 | Childers ......................... 422/26 |

(Continued)

FOREIGN PATENT DOCUMENTS

| AT | 005 071 | 3/2002 | ............. B29B 11/14 |
| DE | 100 19 047 | 10/2001 | ................ A61L 2/20 |

(Continued)

OTHER PUBLICATIONS

EPO Search Report for corresponding application No. EP11192226, dated Apr. 20, 2012 (6 pgs).

(Continued)

*Primary Examiner* — Monzer R Chorbaji
(74) *Attorney, Agent, or Firm* — Hayes Soloway P.C.

(57) ABSTRACT

A vaporizer for the sterilization of containers, includes a housing, a first opening arranged in the housing for supplying a gaseous medium to the housing, an injection device for injecting into the housing a substance which contains hydrogen peroxide ($H_2O_2$). A heating device is arranged inside the housing for vaporizing the hydrogen peroxide, and a second opening is arranged in the housing for discharging a mixture of the gaseous medium and the vaporized hydrogen peroxide from the housing. The injection device extends in a longitudinal direction perpendicular to a plane of the heating device and the first opening is adjoined by a pipe section which extends at least partially in a longitudinal direction (L) of the injection device, wherein the injection device runs at least partially inside the pipe section.

24 Claims, 4 Drawing Sheets

(56) References Cited

U.S. PATENT DOCUMENTS

| | | | |
|---|---|---|---|
| 5,879,648 A | 3/1999 | Hada et al. | 422/304 |
| 6,077,480 A | 6/2000 | Edwards et al. | 422/28 |
| 6,349,887 B1 * | 2/2002 | Pyo | 239/137 |
| 6,736,379 B1 | 5/2004 | Wegner et al. | 261/127 |
| 6,746,652 B2 | 6/2004 | Khorzad et al. | 422/305 |
| 6,786,249 B2 * | 9/2004 | Armbruster et al. | 141/92 |
| 6,899,856 B2 | 5/2005 | Itoh et al. | 422/305 |
| 2004/0089369 A1 | 5/2004 | Armbruster et al. | 141/82 |
| 2007/0045216 A1 | 3/2007 | Gami et al. | 215/42 |
| 2009/0126518 A1 | 5/2009 | Meinzinger et al. | 73/865.9 |

FOREIGN PATENT DOCUMENTS

| | | | | |
|---|---|---|---|---|
| DE | 100 40 861 | | 3/2002 | A61L 2/20 |
| DE | 20 2007 009 983 | | 10/2007 | B65D 1/00 |
| DE | 10 2007 033 621 | | 1/2009 | B65D 1/02 |
| EP | 0 243 003 | | 10/1987 | A61L 2/20 |
| EP | 0243003 | A3 | 10/1987 | A61L 2/20 |
| EP | 0 991 434 | | 4/2000 | A61L 2/20 |
| IT | RM20070552 | | 1/2008 | B65D 1/02 |
| JP | 2001-276189 | | 10/2001 | A61L 2/20 |
| JP | 2002-531260 | | 9/2002 | B05B 7/06 |
| JP | 2007-020744 | | 2/2007 | A61L 2/20 |
| WO | WO 00/33967 | | 6/2000 | B05B 7/00 |
| WO | WO 03/006075 | | 1/2003 | A61L 2/00 |
| WO | WO 03/006075 | A1 * | 1/2003 | A61L 2/00 |
| WO | WO 2007/003313 | | 1/2007 | A61L 2/20 |
| WO | WO 2009/053921 | | 4/2009 | B65D 1/02 |

OTHER PUBLICATIONS

Chinese Office Action issued in corresponding application No. 200880104453.1, dated Aug. 3, 2012 (7 pgs).

Office Action issued in corresponding Japanese Patent Application No. 2010-517370, with English translation, dated Sep. 25, 2012, 6 pgs.

International Search Report received in Applicants' underlying PCT Application Serial No. PCT/EP2008/059421 and English translation, dated Sep. 2, 2010.

* cited by examiner

VAPORIZER FOR STERILIZATION OF PLASTIC CONTAINERS

BACKGROUND OF THE INVENTION

The present invention relates to a vaporizer for the sterilization of containers and in particular plastic containers. Such vaporizers are known from the prior art. Usually hydrogen peroxide ($H_2O_2$) is vaporized within the vaporizer and is guided together with a supplied air flow into a container that is to be sterilized. By virtue of this introduction of the mixture into the container, the internal wall thereof can be cleaned and/or sterilized.

In such vaporizers, however, it is necessary to regulate precisely the quantity of $H_2O_2$ that is to be injected or supplied to the container in each case, and to ensure that in each case the same quantity of $H_2O_2$ is supplied for each container.

WO 2007/003313 discloses a method and an apparatus for monitoring a vaporizer. In this method, a fluid is applied to a heated heating element and is vaporized, and provided to the side of this vaporizer is a pipeline through which heated and sterile air is introduced into the vaporizer or the housing thereof from the side. The air flow is thus conveyed here perpendicular to the direction of injection of the hydrogen peroxide. This apparatus allows an effective supply of vaporized hydrogen peroxide into the container. Due to the nature of the supply, however, an exact regulation of the precise quantity of hydrogen peroxide is possible only with difficulty.

DE 100 40 861 A1 describes an apparatus for sterilizing packagings using hydrogen peroxide. Here, the hydrogen peroxide is passed over a hot surface in the longitudinal direction. In this way, the carrier gas containing the hydrogen peroxide in mist form is vaporized already at this hot surface. Also in this apparatus, a precise regulation of the supplied quantity of hydrogen peroxide is possible only with difficulty.

EP 0 991 434 B1 discloses a multiple flashpoint vaporizing system. Again, both hydrogen peroxide and a carrier gas are introduced into a vaporizer, wherein the carrier gas here too flows transversely relative to the direction of injection of the hydrogen peroxide.

U.S. Pat. No. 5,879,648 describes an apparatus for disinfecting containers. Therefore hydrogen peroxide and, via openings running in parallel, a gas are introduced into a vaporizer. In this apparatus, too, a precise regulation of the mixture passing from the vaporizer into the containers is possible only with difficulty.

The object of the present invention is therefore to provide a vaporizer which allows a very precise regulation of the hydrogen peroxide/gas mixture exiting therefrom.

SUMMARY OF THE INVENTION

The vaporizer according to the invention for the sterilization of containers comprises a housing and a first opening arranged in the housing for supplying a gaseous medium to the housing. Also provided is an injection device for injecting into the housing a substance which contains hydrogen peroxide. Also arranged inside the housing is a heating device for vaporizing the hydrogen peroxide. Also provided is a second opening arranged in the housing for discharging a mixture of the gaseous medium and the vaporized hydrogen peroxide from the housing. According to the invention, a longitudinal direction of the injection device extends perpendicular to a plane of the heating device and the first opening is adjoined by a pipe section which extends at least partially in a longitudinal direction of the injection device, wherein the injection device runs at least partially inside this pipe section.

In a further embodiment according to the invention, a longitudinal direction of the injection device extends perpendicular to a plane of the heating device and the first opening is adjoined by a pipe section which extends at least partially in a longitudinal direction of the injection device, wherein the pipe section extends at least partially inside the housing.

The injection device is preferably a lance-shaped injection device and the longitudinal direction of the injection device is defined by the longitudinal direction of this lance. The injected substance is preferably hydrogen peroxide. This can be injected both in liquid form and in a mist-type consistency. However, injection devices other than lance-shaped injection devices would also be conceivable. In the case of injection devices configured differently, the longitudinal direction thereof is also defined by the flow direction of the $H_2O_2$ upon exiting through a nozzle of the injection device.

The plane of the heating device is understood for example to mean the plane of a heating plate on which the hydrogen peroxide impinges. An extension of the longitudinal direction of the injection device perpendicular to this plane is understood to mean that the angle between this plane and the longitudinal direction is greater than 75°, preferably greater than 80° and particularly preferably greater than 85°. In this way, the hydrogen peroxide exiting from the injection device impinges at least partially also essentially perpendicularly on the heating device. As a result, a uniform vaporization of the hydrogen peroxide takes place on the heating device. By virtue of the arrangement of the injection device inside the pipe section, it is furthermore possible to achieve the situation whereby the gas exiting from the pipe section surrounds the injection device substantially uniformly. In this way, a uniform enrichment of the gas with the hydrogen peroxide can also be achieved. In one advantageous embodiment, the pipe section inside the housing extends at least partially in the longitudinal direction of the injection device. This means that the pipe section starting from the first opening extends inward and in the longitudinal direction of the injection device.

Furthermore, the pipe section preferably has a first exit opening which is arranged in such a way that the gaseous medium exits from the pipe section in a direction parallel to the longitudinal direction. This means that the pipe section which is parallel to the longitudinal direction of the injection direction is an end section of this pipe section.

In a further advantageous embodiment, the pipe section has a second exit opening which is provided between the opening (of the housing) arranged in the housing and the first exit opening. In this way, a partial flow can also be formed in a direction other than the longitudinal direction of the injection device.

Preferably, this second exit opening is arranged in such a way that the gaseous medium exiting through this exit opening flows directly in the direction of the second opening (of the housing). Directly is understood here to mean that the flow flows in the direction of the second opening without being deflected. Preferably, apart from the first opening and the second opening, the housing has no opening through which a gaseous medium can enter the housing or exit from the housing.

Preferably, the first opening in the housing and the second opening in the housing are arranged on opposite sides, for example on opposite sides in the jacket of the housing or else on opposite sides in the longitudinal direction of the injection device.

Advantageously, the first opening is arranged in a circumferential wall of the housing. In a further advantageous embodiment, the pipe section has a curved region, wherein this curved region runs inside the housing in one embodiment.

Preferably, in this embodiment, the second exit opening of the pipe section is arranged in the curved region thereof.

In a further advantageous embodiment, the injection device has an outlet nozzle for the hydrogen peroxide and this outlet nozzle is arranged below the first exit opening of the pipe section. This means that the pipe section and the outlet nozzle do not end at the same height but rather the outlet nozzle is closer to the heating device than the exit opening of the pipe section. In a further embodiment, air guide devices are provided on the pipe section, which air guide devices direct part of the air flow along an inner wall of the vaporizer. Preferably, the pipe section has an inner pipe which concentrically surrounds the injection device, and an outer pipe is provided in at least one region of this inner pipe, wherein the air guide devices are provided between this outer pipe and the inner pipe. In this case, the inner pipe is the pipe section according to the invention.

In a further advantageous embodiment, the injection device and the pipe section are at least partially essentially concentric with one another. Furthermore, with particular preference, the vaporizer or the housing thereof is configured in a substantially rotationally symmetrical manner relative to a central axis.

In a further advantageous embodiment, the second opening of the housing is arranged in a base section of the housing. In this embodiment, the hydrogen peroxide and the gaseous medium are particularly preferably introduced into the housing from above and are removed from below, that is to say through the base section. In this embodiment, the heating device is located between the lid section and the base section. However, the resulting mixture can also be discharged laterally.

In a further advantageous embodiment, the injection device is arranged such that it can rotate relative to the housing. More precisely, the injection device and preferably also the pipe section are stationary and the housing rotates relative thereto. However, it would also be possible to arrange the injection device fixedly on the housing and to arrange the latter in a stationary manner, and to arrange an outlet pipe for discharging the mixture in a manner such that it can rotate relative to the housing.

The present invention also relates to an arrangement for the sterilization of containers and in particular plastic containers, which comprises at least one vaporizer of the type described above. Preferably, this arrangement comprises a heating device for heating the gaseous medium. More precisely, the gaseous medium is heated before it enters the vaporizer.

The present invention also relates to a method for the sterilization of containers, wherein a gaseous medium is introduced into a vaporizer and a substance which contains hydrogen peroxide ($H_2O_2$) is injected by means of an injection device, and wherein this substance is vaporized at a heating device and the resulting mixture of the gaseous medium and the vaporized substance is discharged via a second opening arranged in the housing. According to the invention, the longitudinal direction of the injection device extends perpendicular to a plane of the heating device and the gaseous medium runs within a pipe section at least partially parallel to the longitudinal direction of the injection device, wherein the injection device runs at least partially inside the pipe section.

In a further method according to the invention, the longitudinal direction of the injection device extends perpendicular to a plane of the heating device and the gaseous medium runs within a pipe section at least partially parallel to the longitudinal direction of the injection device, wherein the pipe section extends at least partially inside the housing.

Here, too, the substance is preferably hydrogen peroxide. In the context of the method, a particularly favorable flow guidance of the exiting substance is achieved as a result of the at least partial parallel guidance of the injection device. A discharging of the mixture from the vaporizer with a favorable flow can also be achieved.

BRIEF DESCRIPTION OF THE DRAWINGS

Further advantages and embodiments will emerge from the appended drawings.

In the drawings.

DETAILED DESCRIPTION OF THE INVENTION

Figure 1:
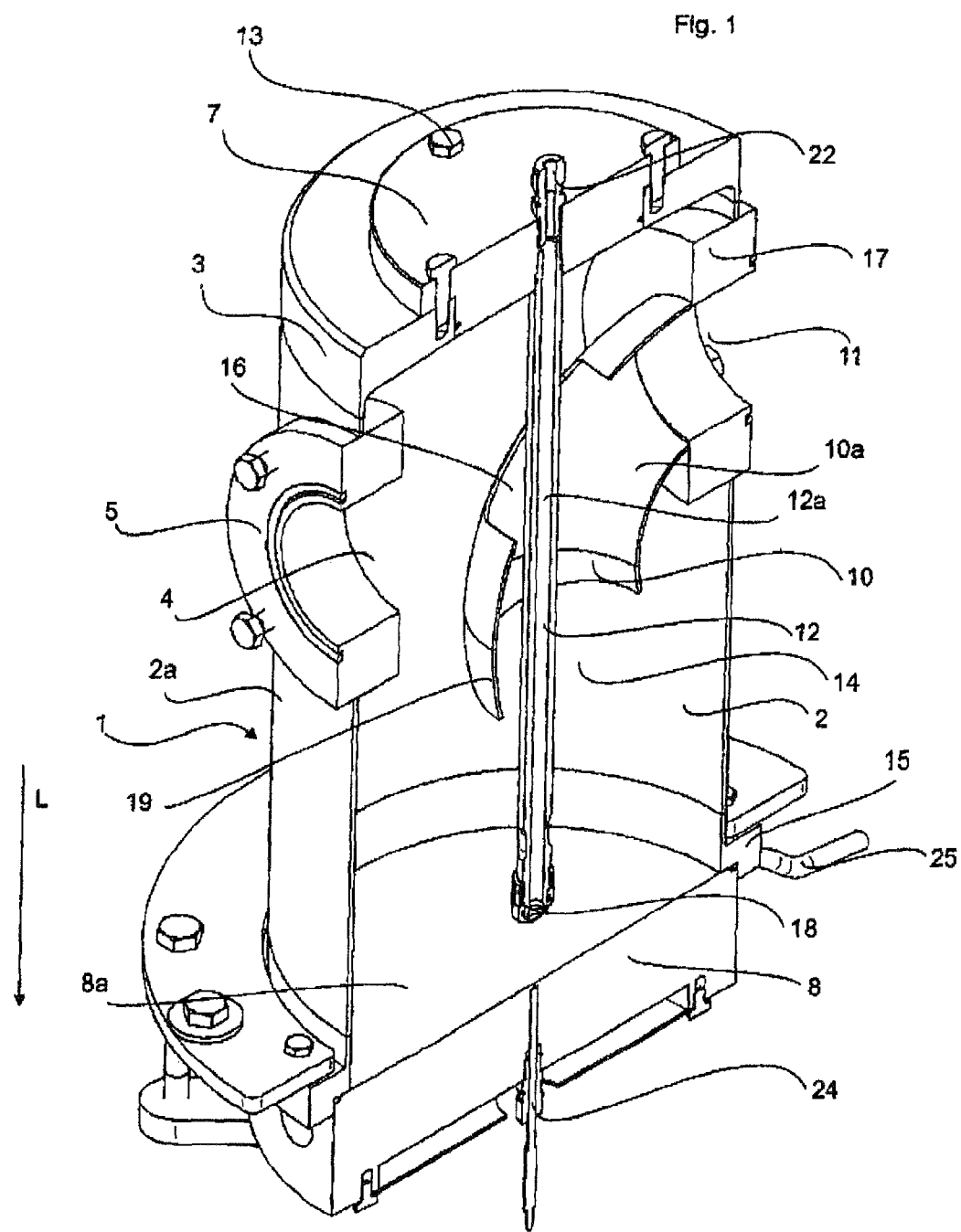
FIG. 1 shows a perspective view of a vaporizer according to the invention.

FIG. 1 shows a vaporizer 1 according to the invention. This vaporizer comprises a housing 2 with a circumferential wall 2a and a lid section 3, which is closed by a lid 7 screwed on using screws 13. In the downward direction, the housing is closed by a heating device 8 or a heating surface 8a. The plane of this heating surface is perpendicular to the plane of the figure. Reference 12 denotes an injection device, the longitudinal direction of which extends perpendicular to the plane of the heating surface 8a. Through this injection device 12, more precisely a channel 12a in the interior of the injection device 12, hydrogen peroxide is passed into the housing 2 and in the direction of the heating device 8. In the embodiment shown in FIG. 1, the injection device 12 is arranged concentric with the circumferential wall 2a. At the lower end, the injection device 12 has a nozzle 18, via which hydrogen peroxide can exit and is sprayed onto the heating surface 8a.

Figure 4:
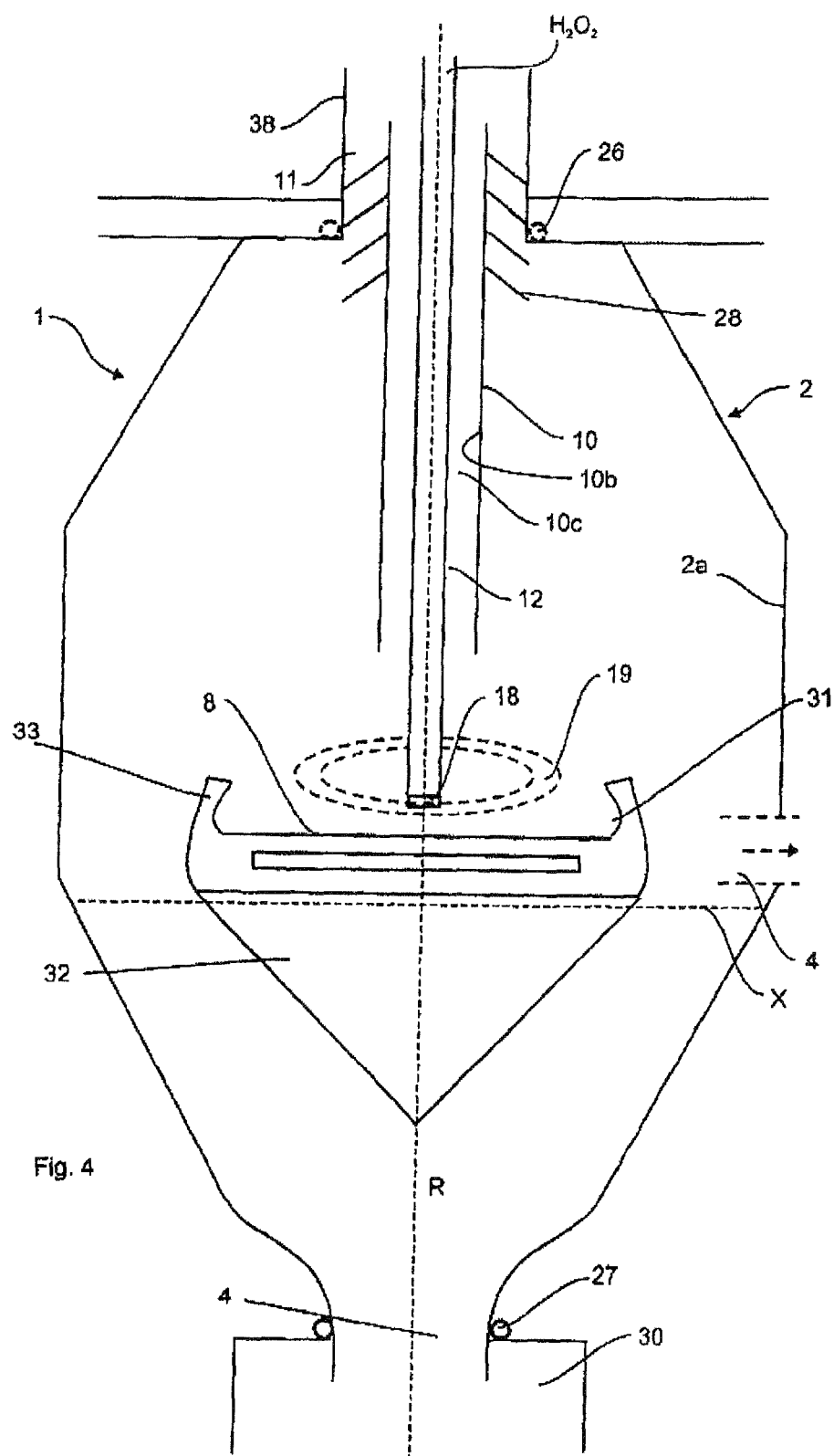
FIG. 4 shows a vaporizer in a further embodiment.

Reference 24 denotes a temperature sensor for determining the temperature of the heating device 8. Provided above the heating device 8 is a flange 15 for attaching the housing 2 to the heating device 8. Like the housing 2, this flange 15 is preferably made from stainless steel. In one preferred embodiment, the heating device 8 is made from aluminum and has side walls at its edges, which side walls do not run in a straight line but rather have an outwardly pointing recess. By virtue of such a recess, the air flow in the area around the heating device 8 can be improved and thus an improved vaporization of the hydrogen peroxide can be achieved. This configuration of the side walls is shown in FIG. 4.

Provided above the heating device 8 is a carrier ring 15, on which in turn the housing 2 is supported. Preferably, this carrier ring 15 is made from a material which has a low heat transfer quotient, so that the housing 2 is not or is not substantially heated by the heat output by the heating device 8.

Reference 11 denotes a first opening (entry opening) in the housing 2, through which the gaseous medium can pass into the interior of the housing 2. The first opening 11 is arranged in a flange 17 which is attached to the housing wall 2a. In the interior of the housing 2, the first opening 11 is adjoined by a pipe section 10. This pipe section 10 has a curved region 10a and a first exit opening 14, through which the gaseous medium can exit. The flow guidance of the heated air therefore takes place partially parallel to the hydrogen peroxide supply through the injection device 12. For this purpose, the air flowing in through the first opening 12 is deflected in the curved section 10a.

Reference 16 denotes a second exit opening in the pipe section 10. On the one hand the injection device 12 passes through this opening. In this way, the injection device can be guided at least partially inside the pipe section 10. In addition, part of the gaseous medium can exit from the pipe section through the second exit opening 6 and can pass in the direction of an exit opening 4. Via the exit opening 4, which is likewise arranged by means of a flange 5 on the housing wall 2a, the gas mixture produced in the vaporizer can be discharged and can then be supplied to the containers to be sterilized.

Figure 2:
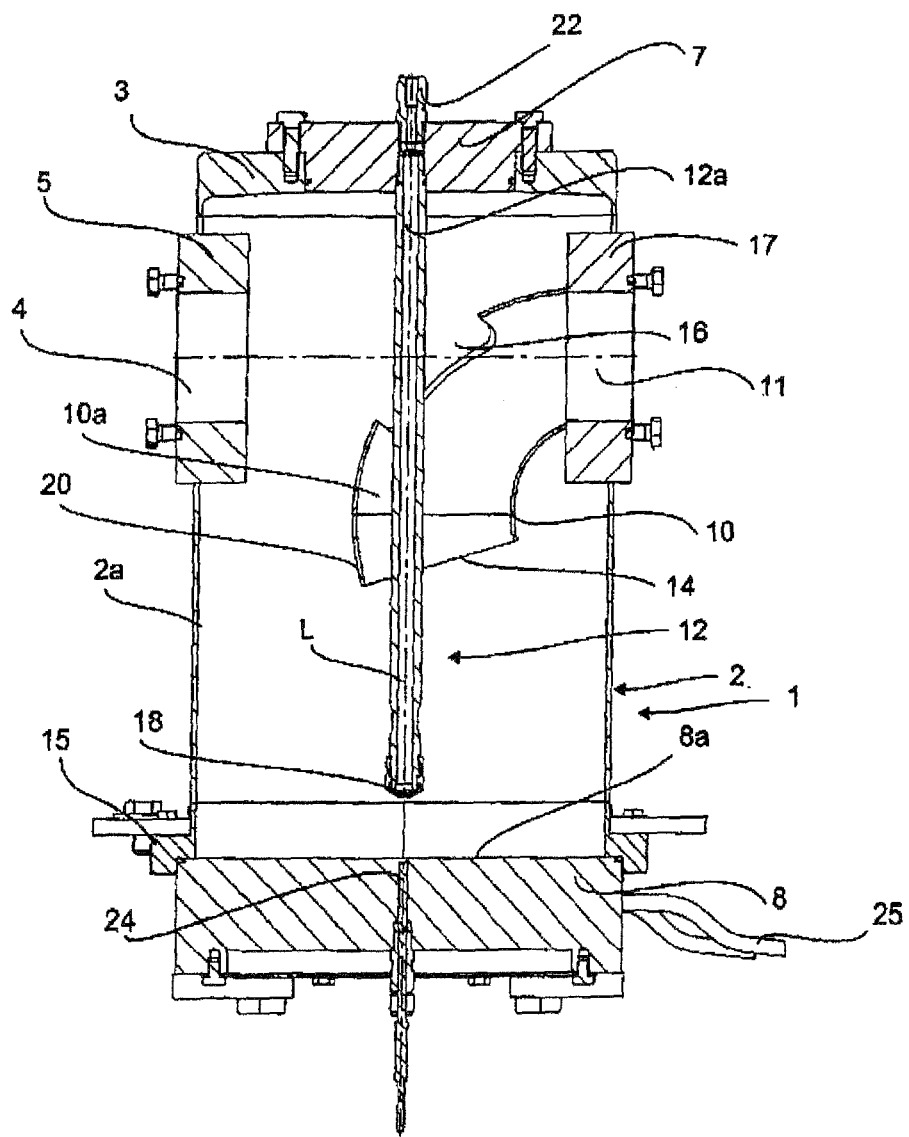
FIG. 2 shows a cross-sectional view of the vaporizer of FIG. 1.

FIG. 2 shows a cross-sectional view of a vaporizer according to the invention. It can be seen that the nozzle 18 of the injection device 12 protrudes much further into the interior of the housing and is arranged much closer to the heating device 8 than the first exit opening 14 of the pipe section 10. In the end section 20 of the pipe section 10, the gaseous medium passing through is not guided precisely in the longitudinal direction but rather is inclined at a certain angle thereto. In this way, a particularly advantageous thorough mixing with the vaporizing hydrogen peroxide is achieved due to corresponding reflections of the gaseous medium at the heating device. More precisely, the gaseous medium passing through the pipe section 10 is guided slightly back again in the direction of the first opening 11. Reference 22 denotes a connection for a hydrogen peroxide supply line. Reference 25 denotes a supply line for a heating medium for the heating device 8.

It can be seen that the second exit opening 16 in the pipe section 10 is configured in such a way that a relatively large portion of this second exit opening 16 is located to the right relative to the injection device 12, that is to say the injection lance 12, and only a small portion is located to the left thereof. In this way, the pipe section inside the housing and thus also the surface thereof can be kept small.

Figure 3:
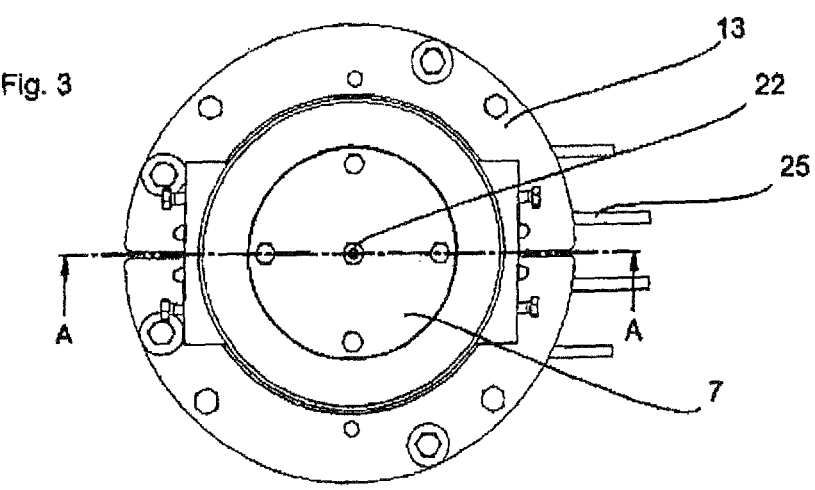
FIG. 3 shows a plan view of a vaporizer according to the invention.

FIG. 3 shows a plan view of the embodiment shown in FIG. 2. It can be seen that the connection 22 and also the entire injection device 12 are essentially concentric relative to the lid 7 and also relative to the housing 2.

FIG. 4 schematically shows two further embodiments of a vaporizer according to the invention. Here, one of these two further embodiments is illustrated by dashed lines. In these embodiments, the first opening 11 is not provided in a side wall of the housing 2 but rather in an upper section or lid. In this way, it is possible also to guide the pipe section 10 in a manner entirely concentric with the injection device 12, without having to provide a curved section. More precisely, no arc of the pipe section is provided in the interior of the housing, but instead any arc is arranged outside the housing 2. The advantage of this embodiment lies on the one hand in the fact that less surface exists inside the vaporizer or the housing 2. Furthermore, by virtue of the essentially symmetrical configuration of the embodiment shown in FIG. 4, it is possible to produce a design of the entire vaporizer which is favorable in flow terms.

The flow is guided directly from the first opening 11 to the second opening 4, which is provided in the base of the housing 2 and below the heating device 8. In the flow path between the first opening 11 and the second opening 4, there is again provided the heating device 8 which serves for vaporizing the hydrogen peroxide.

In this embodiment, the heating device 8 has recesses 31 at the side edges, which recesses bring about an improved air flow as mentioned above.

In this embodiment, the housing 2 with the injection device 10, 11, 12 is stationary and the lower opening 4 rotates. The advantage of this embodiment lies in the fact that the heating device 8 need not be supplied via slip ring carriers. A sealing device 27 which is suitable for such an embodiment will be explained in more detail below in FIG. 5.

Reference 32 denotes a carrier for the heating device, which has a section 33 protruding inward at an angle which is likewise favorable to the flow of the vaporized hydrogen peroxide.

In the further embodiment shown in FIG. 4, the second opening 4 is provided in the side wall 2a. This is shown by the dashed lines in FIG. 4. More precisely, a plurality of second openings 4 are arranged in the side wall 2a, wherein preferably these second openings 4 are provided uniformly in the circumferential direction of the housing 2. Starting from these openings, the individual containers are supplied with the resulting mixture.

In this embodiment (shown by the dashed lines), the housing 2 rotates and the injection device 10, 11, 12 is stationary. The advantage of this embodiment lies in the fact that the heating device is uniformly acted upon by hydrogen peroxide and the seal is functionally integrated. In this embodiment, therefore, only the upper sealing device 26 is provided. In this embodiment, the housing ends directly below the heating device 8, as illustrated by the dashed line X.

The gaseous medium introduced is guided on the one hand in an intermediate space 10c between the injection device 12 and the wall 10b of the pipe section 10 and on the other hand also outside the pipe section 10. For this purpose, deflection devices 28 are provided which deflect the inflowing gaseous medium at an angle and radially outward in the direction of the wall 2a of the housing. The flow conditions in the interior of the vaporizer 1 are also improved as a result.

A further advantage of the second embodiment shown in FIG. 4 lies in the fact that this embodiment can be applied particularly favorably to a treatment carousel. While in the case of the vaporizers in the prior art a plurality of vaporizers are required, wherein the individual vaporizers each sterilize one or two containers, the embodiment shown in FIG. 4 can disinfect a plurality of containers. More precisely, the arrangement shown in FIG. 4 can be arranged such as to partially rotate about the rotation axis R.

In other words, in order to adapt the vaporizer shown in FIG. 4 to a treatment carousel, it is easily possible to separate it into a stationary part and a rotating part in the transition region between an outer pipe 38 and the vaporizer 1. In the embodiment shown in FIG. 4, the injection device 12 and the outer pipe 38 are stationary and the housing 2 including the heating device 8 rotates. In this way, there is no need for a special seal for the supply of hydrogen peroxide, since the corresponding parts are stationary. Furthermore, as mentioned, a central structure for the entire air preparation is possible. The sealing of the housing takes place in the gas region, wherein use may be made of any barrier seals, that is to say seals which use a sealing gas or sealing medium. Reference 26 shows appropriate seals in a highly schematic manner. Unlike in the other embodiments, the sealing here takes place with respect to the resulting gas mixture.

Reference 18 here denotes a nozzle for injecting the hydrogen peroxide. Instead of or in addition to this nozzle, however, use may also be made of an annular nozzle 19 (shown in dashed line). This annular nozzle 19 has openings on its underside, from which the hydrogen peroxide can exit in the downward direction, that is to say in the direction of the heating device 8. Preferably, the hydrogen peroxide exits vertically downward through this nozzle 19. However, it is also possible to combine the individual different embodiments in FIG. 4 with one another, for example the annular nozzle 19 with the openings 4 arranged in the side wall.

Figure 5:
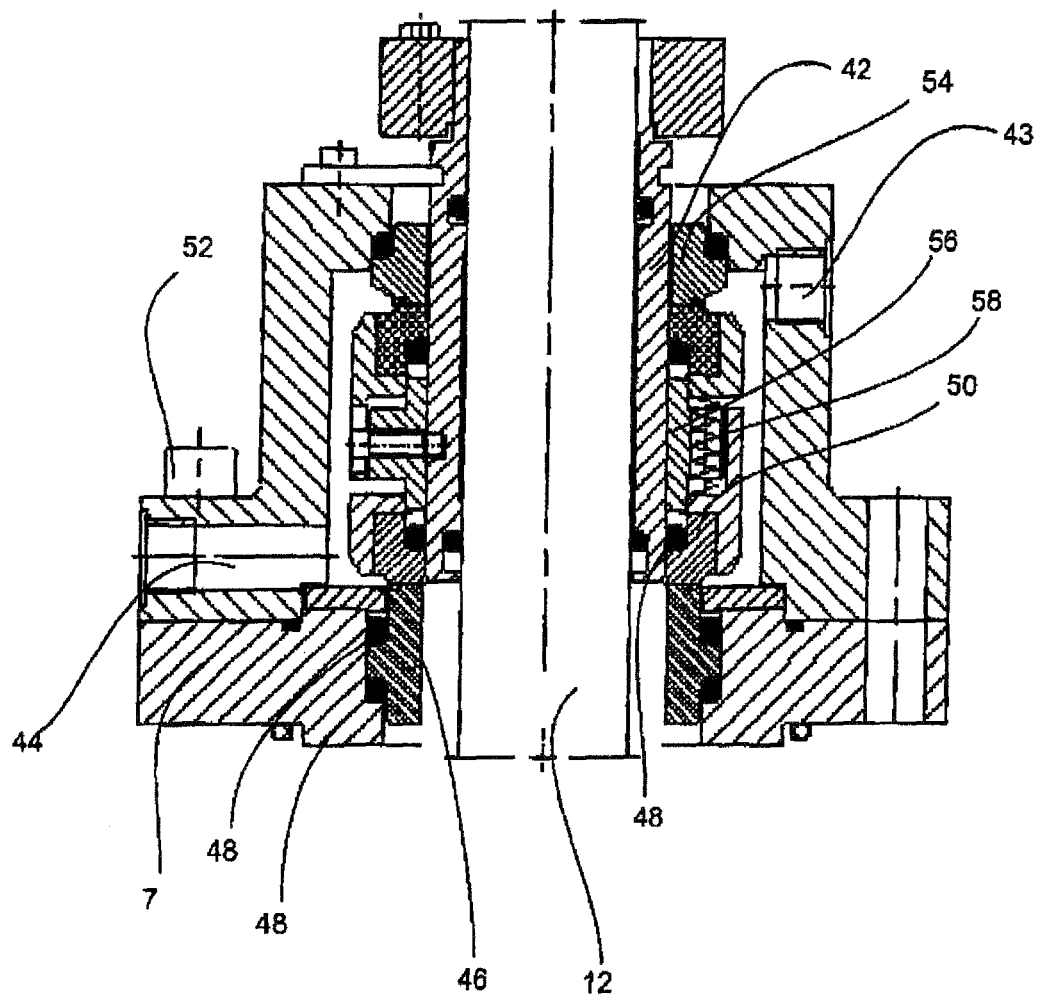
FIG. 5 shows a sealing device for the vaporizer of FIG. 4.

FIG. 5 shows a sealing device 26 for a vaporizer according to FIG. 4. This sealing device 26 is configured in such a way that the injection device 12 is stationary and the housing and/or the lid 7 connected to the housing rotates. More precisely, use is made here of a sliding ring seal 26 with two sliding rings 50, 54. Reference 46 denotes a counter-ring which serves for supporting the lower sliding ring 50. This counter-ring is sealed with respect to the lid 7 by means of two O-rings 48.

A sleeve 42 is arranged on the injection device 12, and two further O-rings 48 are arranged between the injection device 12 and the sleeve 42. Provided between the two sliding rings 50, 54 is an adjusting ring 56 and a plurality of springs (of which only one spring 58 is shown) which load the two sliding rings 50, 54. This adjusting ring 56 is fixedly arranged on the sleeve 42. Reference 43 denotes an inlet for a barrier medium and reference 44 denotes an outlet for the same. This barrier medium, which is particularly preferably sterilized water or air, serves to prevent any unwanted escape of hydrogen peroxide or also of hydrogen peroxide mixture from the vaporizer. In addition, this barrier medium can also be used as a lubricant.

All of the features disclosed in the application documents are claimed as essential to the invention in so far as they are novel individually or in combination with respect to the prior art.

The invention claimed is:

1. A vaporizer for the sterilization of containers, comprising a housing having a first wall, a first opening arranged in the housing for supplying a gaseous medium to the housing, an injection device for injecting into the housing a substance which contains hydrogen peroxide ($H_2O_2$), a heating device arranged inside the housing for vaporizing the hydrogen peroxide, wherein the injection device is arranged to impinge the substance containing the hydrogen peroxide directly onto the heating device, and a second opening arranged in the housing for discharging a mixture of the gaseous medium and the vaporized hydrogen peroxide from the housing, wherein the longitudinal direction (L) of the injection device extends at an angle of greater than 75° to a plane of the heating device onto which the hydrogen peroxide impinges, and the first opening is adjoined by a pipe section which extends at least partially in a longitudinal direction (L) of the injection device, wherein the pipe section comprises a second wall which is distinct from the first wall, which second wall protrudes into the housing, wherein the injection device runs at least partially inside the pipe section, wherein an uniform vaporization of the hydrogen peroxide takes place on the heating device.

2. The vaporizer of claim 1, wherein the pipe section inside the housing extends at least partially in the longitudinal direction (L) of the injection device.

3. The vaporizer according to claim 1, wherein the pipe section, has a first exit opening which is arranged in such a way that the gaseous medium exits from the pipe section in a direction parallel to the longitudinal direction (L).

4. The vaporizer according to claim 1, wherein the pipe section has a second exit opening which is provided between the first opening arranged in the housing and the first exit opening.

5. The vaporizer according to claim 4, wherein the second exit opening is arranged in such a way that the gaseous medium exiting through this exit opening flows directly in the direction of the second opening.

6. The vaporizer according to claim 1, wherein the first opening is arranged in a circumferential wall of the housing.

7. The vaporizer according to claim 1, wherein the pipe section has a curved region.

8. The vaporizer according to claim 7, wherein the second exit opening is arranged in the curved region.

9. The vaporizer according to claim 1, wherein the injection device has an outlet nozzle for the hydrogen peroxide and this outlet nozzle is arranged below the first exit opening of the pipe section.

10. The vaporizer according to claim 1, wherein the first opening is arranged in a lid section of the housing.

11. The vaporizer according to claim 1, wherein the injection device and the pipe section are at least partially essentially concentric with one another.

12. The vaporizer according to claim 1, wherein the second opening is arranged in a base section of the housing.

13. The vaporizer according to claim 1, wherein the entire pipe section is arranged concentric with the injection device.

14. The vaporizer according to claim 1, wherein the injection device is arranged such that it can rotate relative to the housing.

15. The vaporizer according to claim 1, wherein the pipe section is arranged such that it can rotate relative to the housing.

16. An arrangement for the sterilization of containers, comprising at least one vaporizer according to claim 1.

17. The arrangement according to claim 16, comprising a heating device for heating the gaseous medium.

18. The vaporizer according to claim 1, wherein air guide devices are provided on the pipe sections, which direct part of the air flow along an inner wall of the vaporizer.

19. The vaporizer according to claim 1, wherein an outlet pipe for discharging the mixture is arranged in a manner such that it can rotate relative to the housing.

20. The vaporizer according to claim 1, wherein the injection device extends at an angle of greater than 80° to the plane of the heating device onto which the hydrogen peroxide impinges.

21. The vaporizer according to claim 1, wherein the injection device extends at an angle of greater than 85° to the plane of the heating device onto which the hydrogen peroxide impinges.

22. A vaporizer for the sterilization of containers, comprising a housing having a first wall, a first opening arranged in the housing for supplying a gaseous medium to the housing, an injection device for injecting into the housing a substance which contains hydrogen peroxide ($H_2O_2$), a heating device arranged inside the housing for vaporizing the hydrogen peroxide, wherein the injection device is arranged to impinge the substance containing the hydrogen peroxide directly onto the heating device, and a second opening arranged in the housing for discharging a mixture of the gaseous medium and the vaporized hydrogen peroxide from the housing, wherein the longitudinal direction (L) of the injection device extends at an angle of greater than 75° to a plane of the heating device onto which the hydrogen peroxide impinges, and the first opening is adjoined by a pipe section which extends at least partially in a longitudinal direction (L) of the injection device, wherein the pipe section comprises a second wall which is distinct from the first wall, which second wall protrudes into the housing, wherein the pipe section extends at least partially inside the housing, wherein an uniform vaporization of the hydrogen peroxide takes place on the heating device.

23. The vaporizer according to claim 22, wherein the injection device extends at an angle of greater than 80° to the plane of the heating device onto which the hydrogen peroxide impinges.

24. The vaporizer according to claim 22, wherein the injection device extends at an angle of greater than 85° to the plane of the heating device onto which the hydrogen peroxide impinges.

* * * * *

UNITED STATES PATENT AND TRADEMARK OFFICE
CERTIFICATE OF CORRECTION

| | | |
|---|---|---|
| PATENT NO. | : 8,641,982 B2 | Page 1 of 1 |
| APPLICATION NO. | : 12/670600 | |
| DATED | : February 4, 2014 | |
| INVENTOR(S) | : Burgmeier et al. | |

It is certified that error appears in the above-identified patent and that said Letters Patent is hereby corrected as shown below:

In the Claims

Claim 3, Col. 7, line 57 "section, has" should be --section has--

Signed and Sealed this
Twenty-sixth Day of August, 2014

Michelle K. Lee
*Deputy Director of the United States Patent and Trademark Office*